United States Patent
Park

[11] Patent Number: 5,976,870
[45] Date of Patent: *Nov. 2, 1999

[54] ARTIFICIAL LIVER COMPOSED OF A LIVER-SLICE CULTURE APPARATUS

[76] Inventor: Sung-Su Park, Cheonggu Apt. 103-1306, #929 Mok 6-dong, Yangcheon-gu, Seoul, Rep. of Korea, 158-056

[*] Notice: This patent is subject to a terminal disclaimer.

[21] Appl. No.: 09/006,947

[22] Filed: Jan. 14, 1998

Related U.S. Application Data

[63] Continuation-in-part of application No. 08/555,600, Nov. 9, 1995, Pat. No. 5,773,285.

[30] Foreign Application Priority Data

Nov. 9, 1994 [KR] Rep. of Korea .................. 94-29214

[51] Int. Cl.$^6$ ............................. C12M 3/02; C12M 1/16; C12N 5/00
[52] U.S. Cl. ..................... 435/286.5; 435/299.1; 435/1.1; 435/325; 435/394; 435/395; 435/396; 435/174; 435/176; 435/240.23; 435/284; 435/285
[58] Field of Search ................ 435/286.5, 299.1, 435/1.1, 325, 394, 395, 396, 174, 176, 240.23, 284, 285

[56] References Cited

U.S. PATENT DOCUMENTS 5,270,192  12/1993  Li et al. ................................ 435/174
5,773,285   6/1998  Park .................................... 435/286.5

OTHER PUBLICATIONS

Rozga et al. Ann. Surg. 219(5):538–546, May 1994.

*Primary Examiner*—Jeffrey Stucker
*Assistant Examiner*—Phuong T. Bui
*Attorney, Agent, or Firm*—Anderson Kill & Olick

[57] ABSTRACT

Disclosed is an improved artificial liver comprising a static liver-slice culture apparatus which is much more effective than a conventional hepatocyte bioreactor in removing toxins present in the plasma of a patient suffering from hepatic failure.

7 Claims, 3 Drawing Sheets

ARTIFICIAL LIVER COMPOSED OF A LIVER-SLICE CULTURE APPARATUS

RELATED APPLICATIONS

This is a continuation-in-part of application Ser. No. 08/555,600 filed on Nov. 9, 1995 now U.S. Pat. No. 5,773,285.

FIELD OF THE INVENTION

The present invention relates to a bioartificial liver support system for a patient suffering from clinical hepatic failure. Specifically, it pertains to a bioartificial liver support system wherein a liver-slice culturing apparatus is used as a bio-reactor to remove toxins from the plasma of a hepatic failure patient.

BACKGROUND OF THE INVENTION

Acute hepatic failure resulting from a variety of causes has been reported to afflict approximately 2,000 pediatric and adult patients per year in the United States (Berk, P. D. and Popper, H., *American Journal of Gastroenterology*, 69, 349–400(1988)). In spite of the understandings gained by determining the inciting etiology in 60–80% of hepatic failure cases, treatment of this disease still focuses on patient stabilization and expectant management until either the patient's liver recovers or liver transplantation is carried out. It is reported that liver transplantation has increased the survival rate of fulminant hepatic failure patients from less than 20% to greater than 50% (Tygstrup, N. and Ranek, L., *Seminar Liver Disease*, 6, 129–137(1986)); Schafer, D. F. and Shaw, B. W. Jr., *Seminar Liver Disease*, 9,189–194 (1989); Campbell, D. A. Tr. et al., *American Surgeon*, 8, 546–549(1991); Isai, H. et al., *Transplantation Proceeding*, 24, 1475–1476 (1992)).

However, it is difficult to obtain a timely donor liver, and a patient waiting for a donor liver requires an extracorporeal liver support system until a new liver is procured. Such system renders the patient stable and increases the survival rate after the transplantation.

For many years, it has been assumed that the vast majority of toxins which cause hepatic coma are small dialyzable molecules. As a result, most liver support systems and therapeutic regimens used in the past have relied mainly on blood detoxification. However, the pathogenesis of acute hepatic failure is complex and many investigators have suggested that isolated viable hepatocytes be used in the construction of a liver support system not only to provide detoxification but also to restore missing synthetic functions of the liver. In line with this suggestion, a conventional artificial liver has been designed based on the use of a bioreactor containing isolated living hepatocytes packed typically in hollow fiber membranes.

Although isolated hepatocytes used in the conventional bio-reactor exhibit some desirable effects arising from intercellular interactions thereamong, such effectiveness is limited due to the lack of cell to connective interactions which characterize the liver in its in vivo state. Therefore, the conventional artificial liver has been found to be only marginally effective in various clinical studies. Accordingly, an artificial liver device comprising liver slices or tissues has been proposed by some investigators (Nose, Y. et al., *ASAIO Trans.*, 358–362(1963)); Soyer, T. et al., *Surg. Forum*, 23, 346(1972); Soyer, T. et al., *Am. J. Surg.*, 126, 20–24(1973); Kimura, K. et al., *Artif. Organs*, 4, 297–301(1980)), but the development of an efficient system based on the use of liver slices or tissues has not been successful, mainly due to difficulties in maintaining liver slices viable and functional in such a system.

SUMMARY OF THE INVENTION

Accordingly, it is a primary object of the present invention to provide a bioartificial liver support system which uses liver slices maintained in a liver-slice culture apparatus.

In accordance with the present invention, there is provided a bioartificial liver support system which is composed of a plasma separator for separating a blood stream taken from a hepatic failure patient into a plasma stream and a blood cell stream and a liver-slice culture apparatus used as a bio-reactor to detoxify the plasma stream, said apparatus comprising:

(a) a sealable chamber having an inlet and an outlet for an oxygenated gas, and a vertical or downwardly slanted inner wall;

(b) a mesh mounted on the inner wall so as to form a layer of open space having a substantially uniform thickness of 1 to 5 mm between the mesh and the inner wall;

(c) a plurality of animal liver slices held on the mesh; and (d) means for supplying the plasma stream to an upper portion of said layer of open space.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE INVENTION

Figure 1:
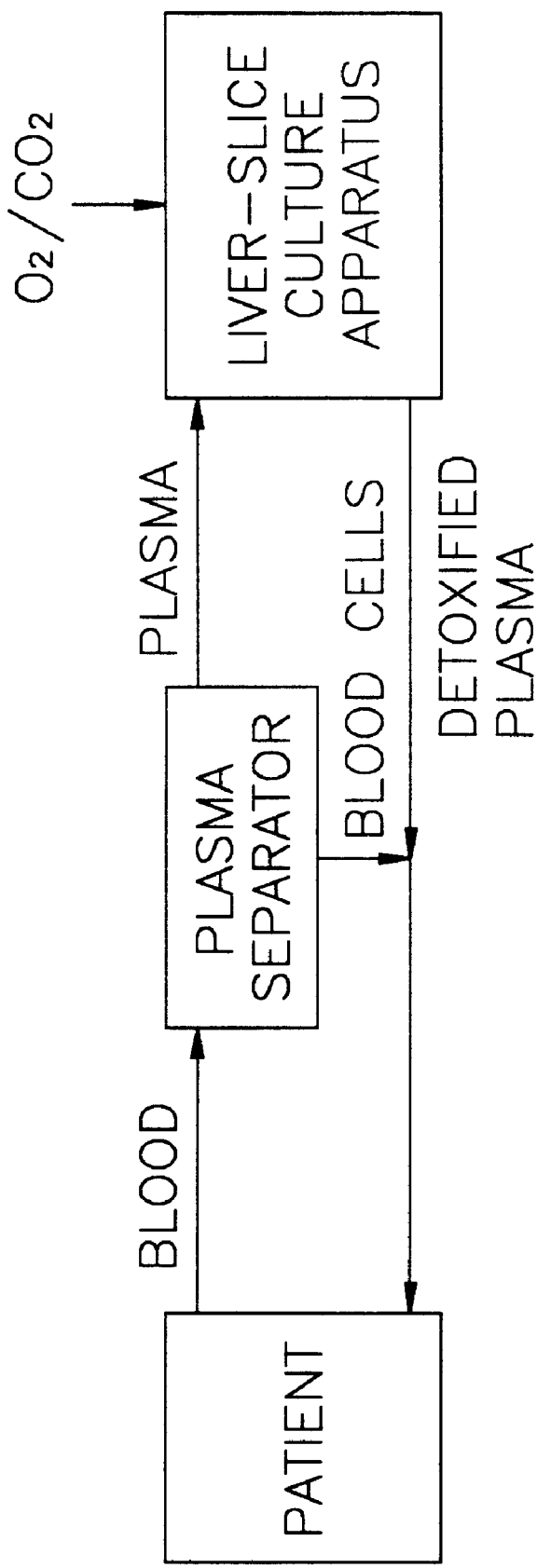
FIG. 1 shows a schematic diagram of the artificial liver support system of the present invention.

In accordance with the present invention, there is provided an improved artificial liver for treating a hepatic failure patient which comprises a plasma separator for separating the patient's blood into plasma and blood cells, a liver-slice culture apparatus for detoxifying the patient's plasma, means for circulating the patient's blood to the plasma separator and means for recirculating the detoxified plasma and the blood cells back to the patient.

The liver-slice culture apparatus of the present invention comprises a sealable chamber; animal liver slices; a mesh for holding the animal liver slices thereon, which is so mounted on a vertical or downwardly slanted inner wall of the chamber that a layer of open space having a substantially uniform thickness is formed between the mesh and the inner wall; and means for supplying plasma of a hepatic failure patient to an upper portion of the layer of open space.

In the above liver-slice culture apparatus, the term "ertical or downwardly slanted inner wall of the chamber" is intended to mean any surface in the chamber which is suitable for mounting the mesh; it may be an inner side-wall of the chamber having the shape of a cylinder, pillar, inverted pyramid or funnel, or a flat or curved plate installed inside the chamber. Although various methods may be employed to secure liver slices on a mesh, it is preferred to place liver slices on a mesh mounted on a downwardly slanted surface having an inclination of 20° to 80°, preferably, 60°. In order for better control of the uniformity of the plasma flow through the layer of open space between the mesh and the inner wall, the thickness of the layer of open space preferably ranges from 1 to 5 mm, more preferably from 2 to 3 mm.

Liver slices used in the liver-slice culture apparatus of the present invention may be obtained from the liver of a suitable animal, e.g., a rabbit, pig, dog and human, depending on the intended use of the inventive bioartificial liver. Also, they may be of any shape which is suitable for maintaining the viability and essential functions thereof in the inventive apparatus. However, in order to minimize the risk of necrosis, the liver slices used in accordance with the present invention are preferred to have a thickness ranging from 10 to 2,000 μm, more preferably from 100 to 500 μm.

It is also desirable to stabilize the liver slices used in the artificial liver of the invention before subjecting them to the task of detoxifying the plasma of a hepatic failure patient. For this purpose, the liver slices are preferably cultured in the liver-slice culture apparatus of the present invention under the supplies of a liquid culture medium and an oxygenated gas, wherein the liquid culture medium is supplied to the layer of open space between the mesh and the inner wall at regular intervals so that each of the liver slices is exposed alternately to the medium and the gas at an exposure time ratio ranging from 1:2 to 1:4, preferably 1:2.5 to 1:3.5. This pre-culturing procedure to stabilize the liver slices enhances the functional characteristics thereof during the step of detoxifying the patient's plasma. After draining the liquid culture medium, the liver slices thus stabilized are washed with physiological saline and used in the liver-slice culture apparatus of the present invention as follows.

A blood stream taken from a hepatic failure patient is sent to a plasma separator to obtain a plasma stream and a blood cell stream. The plasma stream is then led, preferably via a plasma reservoir, to an upper portion of the layer of open space formed between the mesh and the inner wall. In order to achieve a uniform flow of the plasma over the entire width of said layer, it may be preferred to distribute the plasma flow by way of using a plasma distributor which has a bottom slit aligned with, and extending over the length of the top portion of said layer of open space. In the liver-slice culture apparatus of the present invention, the plasma flows downward through the layer of open space, thereby bringing the liver slices mounted on the mesh into contact with the plasma. Accordingly, the rate of the plasma flow is preferably controlled so that each of the liver slices is simultaneously exposed to the plasma on one side thereof and to the oxygenated gas on the other. In this arrangement, the liver slices do not suffer from necrosis due to a sufficient oxygen supply from the side exposed to the gas and to the dissolved oxygen in the plasma entering from the other side.

The plasma flow from the plasma separator may therefore be continuously supplied to the liver-slice culture apparatus of the present invention, but in cases when one wishes to further ensure the prevention of necrosis, the plasma may be supplied at regular intervals so that the liver slices are exposed alternately to the plasma and the oxygenated gas at any exposure time ratio which is suitable for the purpose.

The detoxified plasma stream is collected at a bottom portion of the chamber and recirculated, preferably via a second plasma reservoir, to the patient together with the blood cell stream eluting from the plasma separator.

The bioartificial liver of the present invention represented by the schematic diagram of FIG. 1 may further comprise a device for physically removing toxins from the patient's plasma, e.g., a column packed with cation resins, an activated carbon or charcoal. Such a device is preferably located between the plasma separator and the liver-slice culture apparatus. The use of such device in the bioartificial liver of the present invention provides a hybrid liver support system which consists of both biological and mechanical parts.

The bioartificial liver of the present invention may still further comprise an immunological filter inserted at a downstream site from the culture apparatus. The immunological filter is used to eliminate animal liver antigens produced by animal liver slices in the culture apparatus. It consists preferably of a filter, e.g., a nitrocellulose filter, coated with human anti-animal liver antigen immunoglobulin. The human anti-animal liver antigen immunoglobulins may be obtained by in vitro immunization of autologous(hepatic failure patient) or allogenic human lymphatic tissues with animal liver antigens which are obtained by homogenizing the animal liver in normal saline and then collecting a supernatant.

The oxygenated gas used in the inventive artificial liver is preferably a mixture of 95% by volume $O_2$ and 5% by volume $CO_2$, and it is supplied at a pressure ranging from 1 to 10 atm to the chamber through a gas inlet and discharged therefrom through a gas outlet, while controlling the pressure by a pressure controller. A solenoid valve may be coupled with the pressure controller to maintain a set gas pressure. A gas sterilizing device, i.e., a syringe filter having a pore size of about 0.22 μm, is preferably installed in the gas inlet line to filter out microbes, thereby sterilizing the supply gas to the chamber. Another gas sterilizing device is preferably installed in the gas outlet line in order to prevent backflow of microbes in the atmospheric gas.

The bioartificial liver support system of the present invention is much more effective than a conventional artificial liver based on isolated hepatocytes in removing toxins from the plasma of a hepatic failure patient, thereby increasing the survival rate of the patient. Clinical studies show that the levels of various toxic substances, particularly that of ammonia, decrease markedly when the inventive system is applied to an acute hepatic failure model. The present invention thus provides, for the first time, an efficient bioartificial liver which successfully utilizes liver slices instead of hepatocytes in detoxifying the blood of a hepatic failure patient.

The following Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

EXAMPLE 1

Hepatic Failure Model

A Mongol dog, weighing 16 kg, was anesthetized with 15 mg dose of Ketamine and 1.5 g of D-galactosamine/kg body weight was intravenously injected in the brachial vein. 24 hours after the D-galactosamine injection, the experimental dog exhibited symptoms of hepatic encephalopathy; drowsiness, lethargy and loss of ability to perform routine tasks and disorientation. The dog was in a full coma state after 29 hours from the D-galactosamine injection, and died 45 minutes thereafter. The in-blood levels of glucose, ammonia, fibrinogen, total bilirubin, GOT, GPT, LDH, sodium potassium and calcium were determined at each of the above stages and the results are summarized in Table 1.

TABLE 1

|  | Glucose mg/dl | NH₃ ug/dl | Fibrinogen mg/dl | T-bilirubin mg/dl | GOT I.U/l | GPT I.U/l | LDH I.U/l | Na mEq/l | K mEq/l | Cl mEq/l | Ca mg/dl |
|---|---|---|---|---|---|---|---|---|---|---|---|
| Before injection | 89 | 49 | 330 | 0.1 | 22 | 35 | 260 | 140 | 304 | 109 | 8.7 |
| Onset of hepatic coma | 28 | 562 | 60 | 0.8 | 5,773 | 3,055 | 3,427 | 149 | 5.4 | 114 | 7.0 |
| 45 min after BAL without bioreactor | 8 | 660 | 49 | 0.8 | 7,240 | 3,814 | 3,580 | 148 | 6.7 | 120 | 6.9 |

The above experiment was repeated several times and it was found that the above results could be reproduced more or less consistently; an experimental Mongol dog fell into a coma state 28–30 hours after the D-galactosamine injection, and died within one hour thereafter.

EXAMPLE 2

Evaluation of Artificial Liver (Step 1) Preparation of a Liver-Slice Culture Apparatus for Bioartificial Liver Treatment A New Zealand white rabbit, weighing 2–3 kg, was sacrificed by an injection of 10 ml of air via the ear vein, the liver was excised and washed with a cold medium having the following composition:

Waymouth MB 752/1 medium(Gibco Co., USA)

10% Fetal bovine serum(Gibco Co., USA)

0.1% Reduced glutathione(Sigma Co., USA)

0.3% Sodium bicarbonate(Merck Co., USA)

0.45% D-glucose(Gibco Co., USA)

Figure 2:
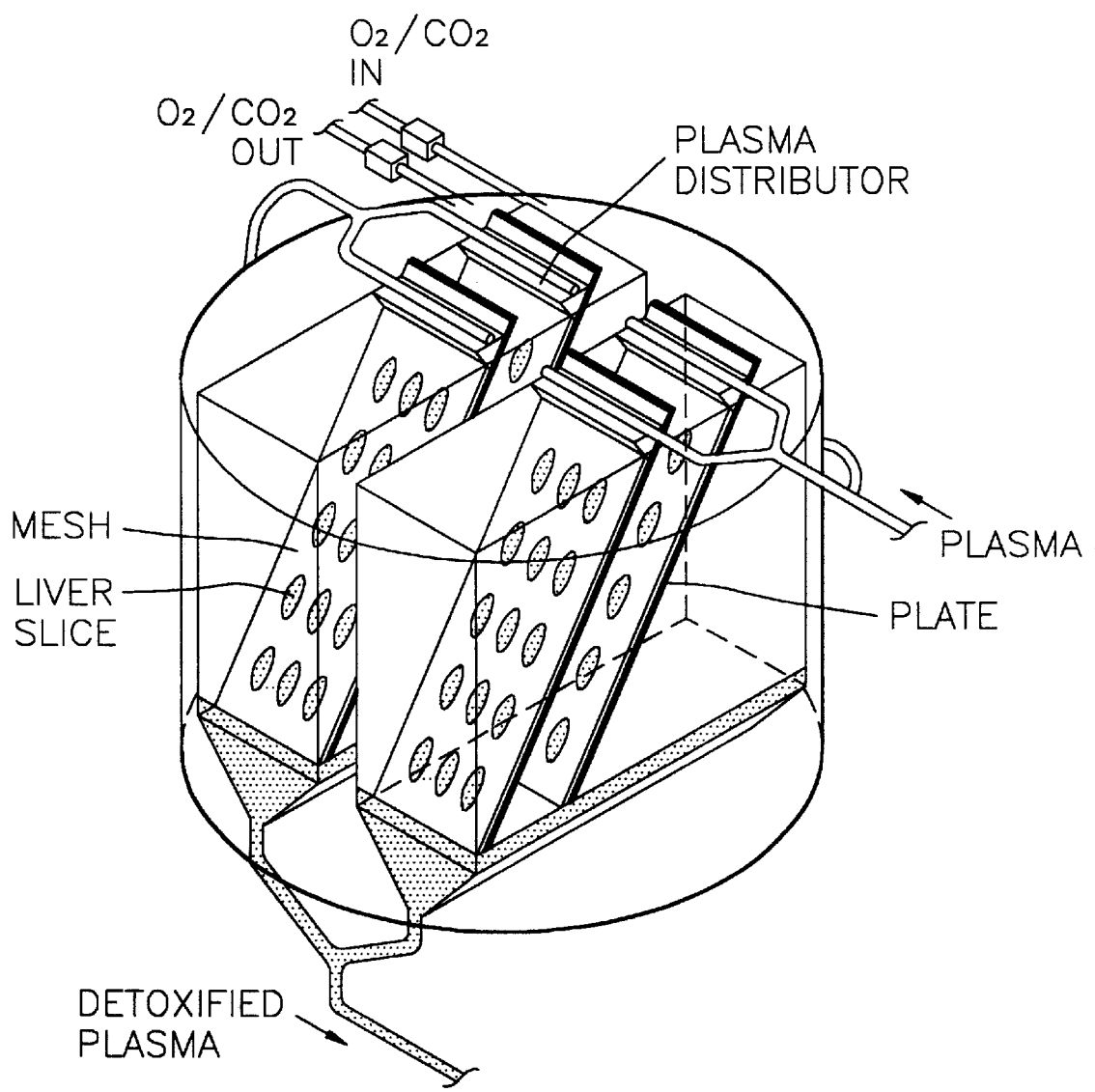
FIG. 2 exhibits an embodiment of the static slice culture apparatus of the present invention.
Figure 3:
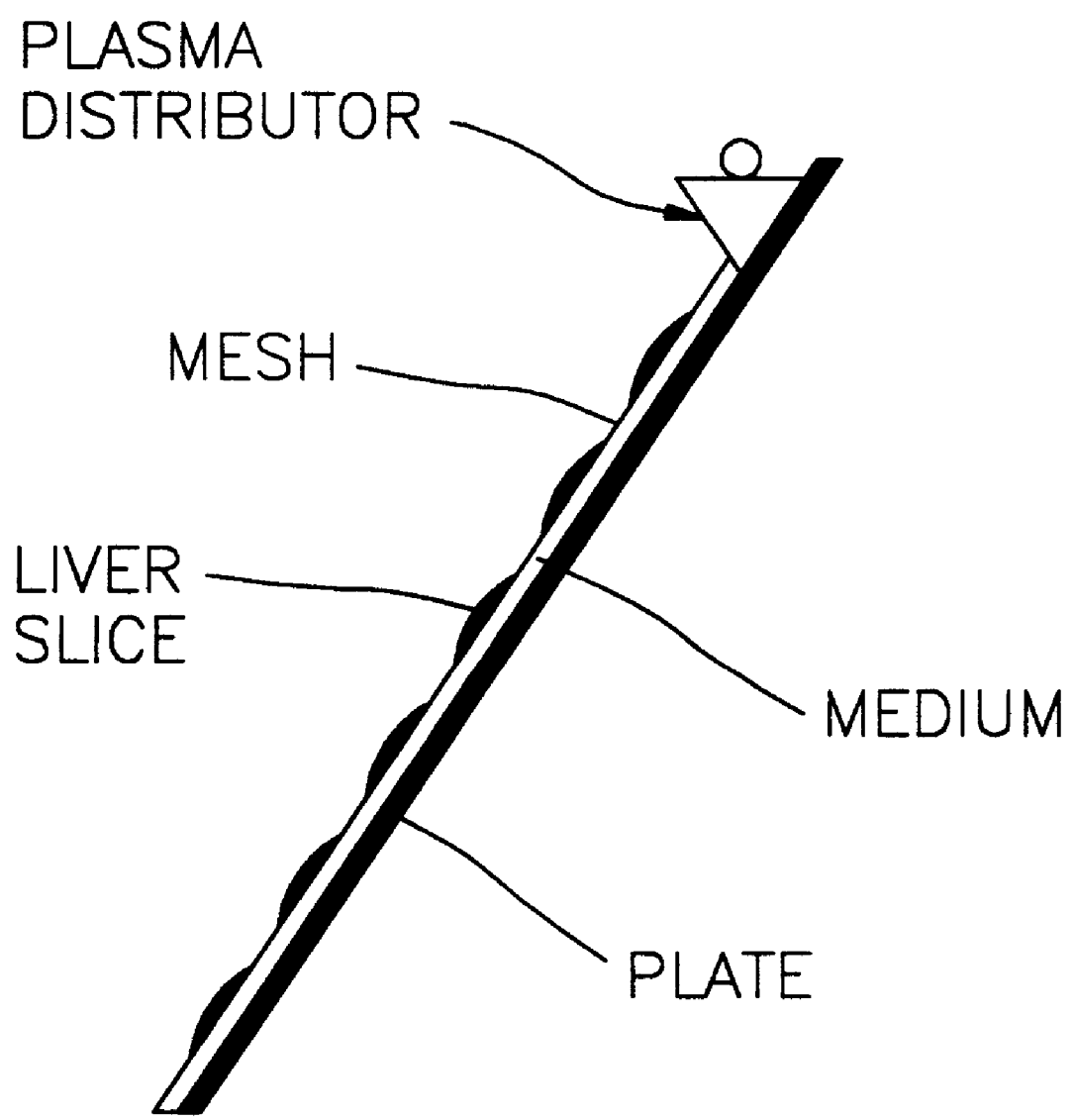
FIG. 3 illustrates a cross-sectional view of an embodiment of the liver slice holder of the static liver-slice culture apparatus of the present invention.

The liver was then sliced in the same culture medium into approximately 260 µm thick and 5×10 mm wide slices, and 15 such slices were mounted onto a holder composed of a stainless steel mesh supported on a 3.5 cm×10 cm stainless steel plate in such a way that there exists a substantially uniform open space of 2 to 2.5 mm between the mesh and the plate. Four such holders each carrying 15 liver slices on the mesh were stacked in a sealable incubation chamber at 60° angle (confer the liver slice holder shown in FIG. 2 and FIG. 3). In this configuration, the number of hepatocytes in the combined liver slices were about $1.8 \times 10^5$. A sterilized oxygenated gas composed of 95% $O_2$ and 5% $CO_2$ was continuously supplied to the chamber maintained at 2.0 atmosphere. The above-mentioned medium was then pumped, at regular intervals, to an upper portion of the open space of each holder in such a way that each of the liver slices on the holders was exposed to the medium and the gas at an exposure time ratio of 1:3. This mode of culturing was conducted for an hour, before draining the medium and washing the liver slices with physiological saline. The liver-slice culture apparatus thus prepared was configured in the arrangement shown in FIG. 2 and employed in the following bioartificial liver treatment.

(Step 2) Preparation of a Hepatic Failure Model

A Mongol dog, weighing 15 kg, was anesthetized with a 10 mg dose of ketamine and 1.5 g of D-galactosamine/kg body weight was intravenously injected in the brachial vein. 24 hours after the D-galactosamine administration, the experimental dog showed drowsiness, lethargy, and gross deficits in ability; symptoms of hepatic encephalopathy.

6 hours thereafter, or 30 hours from the D-galactosamine administration, the animal was in a full coma state. The comatose dog was immediately subjected to the bioartificial liver treatment described below.

(Step 3) Bioartificial Liver (BAL) Treatment

The femoral artery of the hepatic failure dog prepared in Step 2 was connected to a plasma separator using 14-gauge catheters, and Heparin(100 U/kg) was administered to the dog. The blood flow from the dog was separated into plasma and blood cells. The plasma was collected in a plasma reservoir and the collected plasma was circulated at a rate of 30 ml/min. with a peristaltic infusion pump to the liver-slice culture apparatus prepared in Step 1. The plasma detoxified by the treatment with liver slices was collected in a second reservoir and pumped therefrom, together with the blood cells separated at the plasma separator, to the femoral vein of the dog using catheters. During this bioartificial treatment, neither medication nor resuscitation treatments were provided to the dog in order to accurately evaluate the efficiency of the artificial liver.

The experimental dog survived 6 hours after the initiation of the artificial liver treatment, 5 hours longer than the base case determined in Example 1. In order to measure the efficacy of the artificial liver in quantitative terms, hourly blood samples were taken to determine time-dependent variations in the levels of LDH, ammonia, AST/ALT(GOT/GPT), total bilirubin, prothrombin time(PT), fibrinogen, Na, K, Ca, and glucose. The results are listed in Table 2.

TABLE 2

|  | Glucose mg/dl | NH₃ ug/dl | Fibrinogen mg/dl | T-bilirubin mg/dl | GOT I.U/l | GPI I.U/l | LDH I.U/l | Lactate mmol/l | Na mEq/l | K mEq/l | Cl mEq/l | Ca mg/dl |
|---|---|---|---|---|---|---|---|---|---|---|---|---|
| Before injection | 93 | 138 | 118 | 0.1 | 36 | 22 | 347 | 3.4 | 147 | 5.9 | 111 | 9.0 |
| Onset of heptic coma | 43 | 538 | 357 | 0.9 | 4,263 | 7,072 | 1,786 | 5.0 | 152 | 4.2 | 115 | 9.2 |
| 1 hr after BAL | 35 | 394 | 243 | 0.1 | 3,272 | 5,591 | 1,432 | 3.5 | 148 | 3.8 | 124 | 8.7 |
| 2 hrs after BAL | 25 | 439 | 248 | 0.7 | 3,255 | 5,503 | 1,397 | 2.9 | 150 | 3.7 | 123 | 8.6 |

TABLE 2-continued

|  | Glucose mg/dl | NH₃ ug/dl | Fibrinogen mg/dl | T-bilirubin mg/dl | GOT I.U/l | GPI I.U/l | LDH I.U/l | Lactate mmol/l | Na mEq/l | K mEq/l | Cl mEq/l | Ca mg/dl |
|---|---|---|---|---|---|---|---|---|---|---|---|---|
| 3 hrs after BAL | 19 | 423 | 235 | 0.7 | 3,382 | 5,697 | 1,556 | 2.7 | 151 | 3.8 | 124 | 8.3 |
| 4 hrs after BAL | 13 | 636 | 269 | 0.7 | 3,559 | 5,912 | 1,751 | 2.7 | 153 | 3.8 | 123 | 8.2 |
| 5 hrs after BAL | 7 | 520 | 269 | 1.0 | 4,956 | 7,940 | 2,472 | 4.4 | 157 | 5.1 | 119 | 9.4 |

As the data in Table 2 show, the levels of toxins, particularly that of ammonia, drop markedly after one hour BAL treatment.

CONTROL EXAMPLE

The procedure of Example 1 was repeated using a Mongol dog weighing 16 kg except that the liver-slice culture apparatus was not loaded with liver slices. The experimental dog became fully comatose 29 hours after the D-galactosamine injection, and died 1 hour thereafter. The analytical results of plasma samples taken at various stages are listed in Table 3.

TABLE 3

|  | Glucose mg/dl | NH₃ ug/dl | Fibrinogen mg/dl | T-bilirubin mg/dl | GOT I.U/l | GPT I.U/l | LDH I.U/l | Na mEq/l | K mEq/l | Cl mEq/l | Ca mg/dl |
|---|---|---|---|---|---|---|---|---|---|---|---|
| Before injection | 104 | 54 | 305 | 0.1 | 44 | 23 | 243 | 128 | 5.7 | 110 | 8.8 |
| Onset of hepatic coma | 33 | 420 | 60 | 1.0 | 3,204 | 2,746 | 4,372 | 139 | 7.9 | 128 | 8.1 |
| 1 hr after BAL without bioreactor | 14 | 459 | 33 | 1.0 | 3,800 | 2,906 | 4,854 | 146 | 8.1 | 128 | 7.7 |

The data in Table 3 are comparable with those in Table 1, which verifies the fact that the advantages of using the bioartificial liver of the present invention as shown in Example 2 are not due to some experimental artifacts.

While the invention has been described with respect to the above specific embodiments, it should be recognized that various modifications and changes may be made to the invention by those skilled in the art which also fall within the scope of the invention as defined by the appended claims.

What is claimed is:

1. A bioartificial liver for treating a patient suffering from hepatic failure, of the type having a plasma separator for continuously separating a blood stream taken from the patient into a plasma stream and a blood cell stream, a bioreactor for continuously removing toxic substances from said plasma stream to obtain a detoxified plasma stream, and means for circulating said detoxified plasma stream together with the blood cell stream to the patient, wherein the bioreactor comprises:
   (a) a sealable chamber having an inlet and an outlet for the oxygenated gas, and a vertical or downwardly slanted inner wall;
   (b) a mesh mounted on the inner wall so as to form a layer of open space having a substantially uniform thickness of 1 to 5 mm between the mesh and the inner wall;
   (c) a plurality of animal liver slices held on the mesh; and
   (d) means for supplying the plasma stream to an upper portion of said layer of open space.

2. The bioartificial liver of claim 1 further comprising:
   (e) a plasma reservoir located downstream from the plasma separator, which is in fluid communication with the plasma separator and the chamber; and
   (f) a second reservoir for receiving a detoxified plasma stream from the chamber.

3. The bioartificial liver of claim 1, wherein the animal liver slices are pre-cultured in an environment of an oxygenated gas under the supply of a liquid culture medium at regular intervals so that said slices are exposed alternately to the medium and the gas at an exposure time ratio ranging from 1:2 to 1:4.

4. The bioartificial liver of claim 1, further comprising an immunological filter inserted downstream from the second reservoir, said immunological filter containing human anti-animal liver antigen immunoglobulins.

5. The bioartificial liver of claim 1, further comprising an activated carbon filter inserted between the plasma separator and the plasma reservoir.

6. The bioartificial liver of claim 1, wherein the inner wall is the surface of an inner side-wall of the chamber or a plate mounted inside the chamber, said inner wall having an inclination ranging from 20 to 80°.

7. The bioartificial liver of claim 1, wherein the thickness of the layer of open space is in the range of 2 to 3 mm.

* * * * *